United States Patent [19]

Fry

[11] Patent Number: 4,459,982

[45] Date of Patent: Jul. 17, 1984

[54] SERVO-CONTROLLED DEMAND REGULATOR FOR RESPIRATORY VENTILATOR

[75] Inventor: Stanley E. Fry, Riverside, Calif.

[73] Assignee: Bear Medical Systems, Inc., Calif.

[21] Appl. No.: 417,621

[22] Filed: Sep. 13, 1982

[51] Int. Cl.³ .............................................. A61M 16/00
[52] U.S. Cl. ............................. 128/204.23; 128/205.14
[58] Field of Search ..................... 128/204.21, 204.23, 128/204.24, 205.13, 205.14, 205.15, 205.16, 205.18

[56] References Cited

U.S. PATENT DOCUMENTS

| | | | |
|---|---|---|---|
| 3,903,881 | 9/1975 | Weigl | 128/145.6 |
| 3,905,362 | 9/1975 | Eyrick et al. | 128/145.8 |
| 3,916,888 | 11/1975 | Buck et al. | 128/145.6 |
| 3,916,889 | 11/1975 | Russell | 128/145.8 |
| 3,932,066 | 1/1976 | Eyrick et al. | 417/328 |
| 3,951,137 | 4/1976 | Conkle et al. | 128/204.23 |
| 3,961,627 | 6/1976 | Ernst et al. | 128/145.8 |
| 3,972,327 | 8/1976 | Ernst et al. | 128/145.8 |
| 4,001,700 | 1/1977 | Cook et al. | 328/129 |
| 4,036,221 | 7/1977 | Hillsman et al. | 128/145.6 |
| 4,141,356 | 2/1979 | Smargiassi | 128/145.8 |
| 4,210,136 | 7/1980 | Apple | 128/204.21 |
| 4,357,936 | 11/1982 | Ellestad et al. | 128/204.23 |
| 4,393,869 | 7/1983 | Boyarskey et al. | 128/204.23 |

Primary Examiner—Henry J. Recla
Attorney, Agent, or Firm—Howard J. Klein

[57] ABSTRACT

A mechanism is provided for a respiratory ventilator by which the gas-delivery mechanism of the ventilator can be caused to deliver gas to the patient either at a predetermined flow rate or at a rate directly controlled by the patient's instantaneous demand. The mechanism includes a pressure-responsive device adapted to produce an analog signal indicative of the difference between a reference pressure and the patient's airway proximal pressure. The analog signal has a first polarity when the proximal pressure is less than the reference pressure in response to an inhalation effort, and a second polarity when the proximal pressure is greater than the reference pressure in response to an exhalation effort. A first control mechanism is provided which causes the gas-delivery system to deliver gas at a rate which is proportional to the absolute value of the analog signal when the signal has the first polarity and an absolute value at least equal to a predetermined threshold value. The control mechanism responds to the second polarity of the analog signal by causing the gas-delivery system to recharge itself with a fresh supply of gas. The same gas-delivery mechanism can also be operated in an assist mode to deliver gas at a predetermined flow rate by a second control mechanism responsive to the analog signal.

16 Claims, 1 Drawing Figure

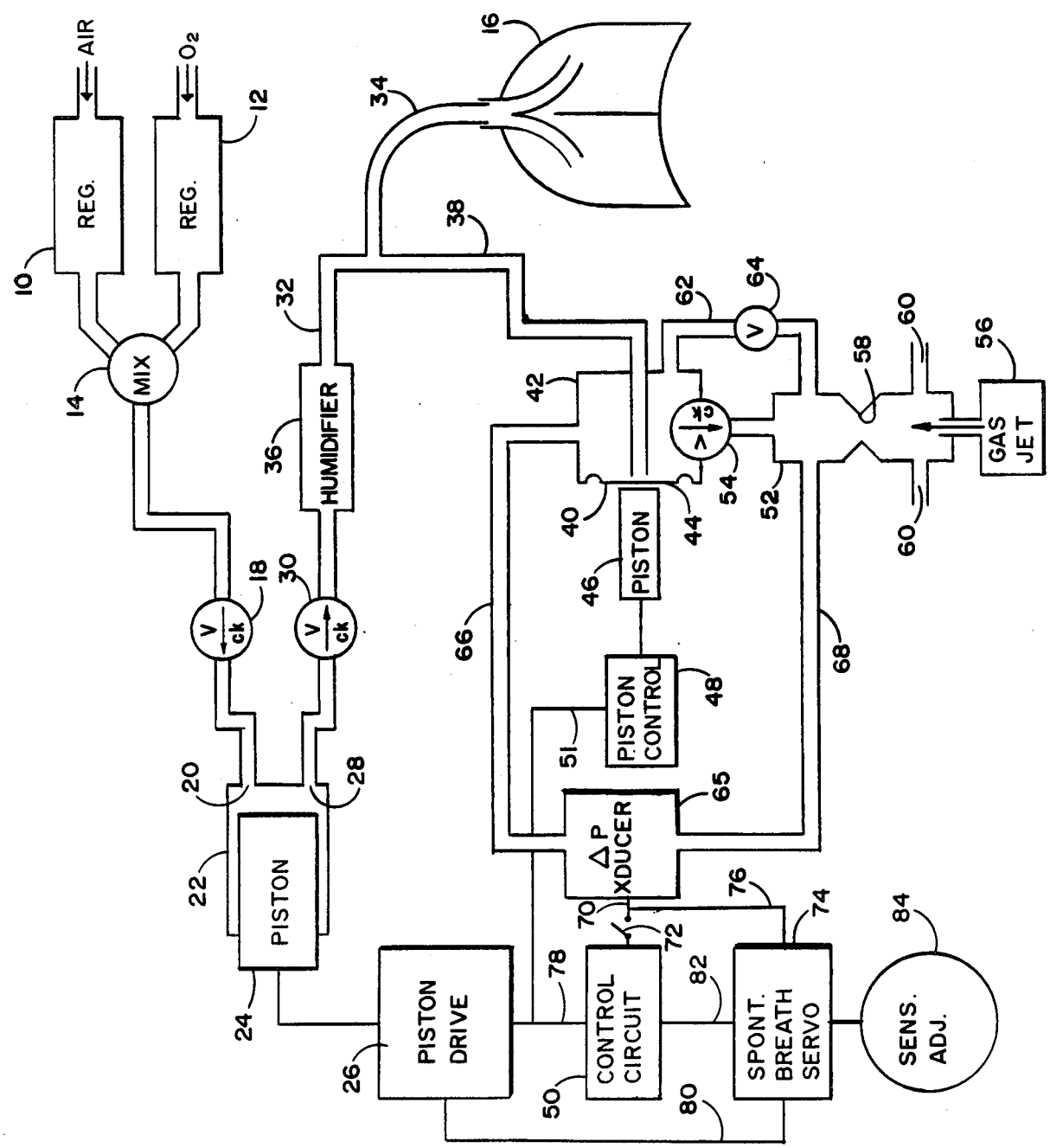

SERVO-CONTROLLED DEMAND REGULATOR FOR RESPIRATORY VENTILATOR

BACKGROUND OF THE INVENTION

This invention relates to the field of medical respiratory ventilators. In particular, it relates to volume ventilators having a breath-assist mode in which the gas-delivery system used to deliver an assisted breath also functions as a demand regulator when the patient breathes spontaneously.

It has become common practice in the field of respiratory ventilators to provide a breath-assist mode in which the patient's breathing activity is monitored, and a volume of air is forced into his lungs when a breath attempt is detected. The assisted breaths are generally provided at a specified rate until the patient is able to breathe on his own.

In most clincal situations, the patient cannot be removed from the respirator abruptly. Rather, he must be "weaned" from the ventilator by gradually increasing the interval between assisted breaths. During this weaning period, it is desirable to allow the patient to breathe spontaneously in the interval between assisted breaths.

It has been found that, rather than have the interval between assisted breaths be measured in absolute time, it is preferable to measure these intervals in terms of the patient's spontaneous breathing rate. Accordingly, during the weaning operation, the ventilator will deliver an assisted breath after a predetermined number of spontaneous breaths, with this number of spontaneous breaths being increased as the weaning process progresses.

A respiratory ventilator which provides this type of weaning capability is described in U.S. Pat. No. 4,141,356 to Smargiassi. While the Smargiassi device is capable of providing both spontaneous breaths and assisted breaths in selectable ratios suitable for accomplishing the weaning function, it does so by means of separate pneumatic circuitry for providing the breathable gas to the patient during a spontaneous breath and during an assisted breath. Specifically, spontaneous breathing is accomplished through a demand regulator which provides gas to the patient at a suitable pressure for spontaneous breathing. Assisted breaths, on the other hand, are provided by a pneumatic piston which is actuated at the appropriate time by an electronic timing circuit which is responsive to the patient's inhalation efforts.

While the system disclosed in the Smargiassi patent is entirely acceptable, it would be desirable to simplify the pneumatic circuitry involved. In particular, means have been sought for eliminating the necessity of a separate pneumatic circuit for delivering spontaneous breaths, thereby using the piston which delivers the assisted breaths also in the role of a demand regulator during spontaneous breathing.

However, in order to accomplish this latter result, it is necessary somehow to provide the piston with means for responding to the patient's instantaneous inhalatory demands, in the same manner as a conventional demand regulator. In other words, the piston must not just be responsive to the initiation of an inhalatory effort, but it also must be capable of delivering gas at a rate which satisfies the patient's demand. Thus, when the patient takes a "deep" breath, indicative of a strong demand for air, the piston must be capable of delivering the breathable gas initially at a rapid flow rate which decreases as the patient's demand is satisfied. Thus, it would be advantageous to provide some means to "slave" the piston's stroke to instantaneous changes in the patient's inhalatory effort; or, in other words, to have the flow produced by the piston be both initiated and controlled by the patient's demand.

The use of an indication of patient demand to initiate the actuation of a gas-delivery system is well-established in the art; and, indeed, is the essence of the assist mode of ventilator operation, as exemplified in the aforementioned Smargiasi patent. Also known in the art are systems whereby the values of gas flow and pressure measurements taken at the patient interface are used to control the action of the gas-delivery system. See for example U.S. Pat. Nos. 3,961,627 and 3,972,327, both to Ernst et al. In such systems, however, the measured parameter is compared, by suitable logic circuitry, with a predetermined reference value for that parameter. While such systems are well-adapted for accurately controlling pressure and or flow-rate regimens in connection with controlled breathing or assisted breathing modes of ventilation, they make no provision for allowing the patient to control his own breathing regimen by responding to instantaneous changes in the patient's demand, as is required in spontaneous breathing. Another approach taken by the prior art is exemplified in U.S. Pat. No. 4,001,700 to Cook et al., and U.S. Pat. No. 4,036,221 to Hillsman et al. In this latter type of device, a desired flow rate versus time waveform is selected, and a control system indicative of this waveform is fed into control circuitry along with the signal from a position transducer, responsive to the position of a gas-delivery piston, so that the position of the piston is continuously adjusted so as to maintain the desired flow of gas in accordance with the selected waveform. However, such a system makes no provision for allowing the piston action to be controlled directly by the patient in accordance with his spontaneous demand.

It can therefore be appreciated from the foregoing that, while the prior art provides various mechanisms for initiating and controlling the actuation of the gas-delivery system in a ventilator, the prior art has not provided means for "slaving" that same gas-delivery system to the patient's instantaneous demand when spontaneous breathing is indicated. Rather, as previously mentioned in connection with the Smargiassi patent, the prior art must resort to a parallel breathing circuit using a separate and discrete demand regulator to accommodate spontaneous breathing.

SUMMARY OF THE INVENTION

The present invention provides a mechanism in a pulmonary ventilator by which the gas-delivery system of the ventilator, be it a piston or bellows, can be caused to deliver gas to the patient either at a predetermined flow rate (in controlled or assisted breathing modes of operation), or at a rate directly controlled by the patient's instantaneous demand when the patient breathes spontaneously.

Broadly, the invention comprises a pressure-responsive device, such as a differential pressure transducer, connected in a patient circuit so that one side of the transducer is receptive to the patient's airway proximal pressure, while the other side of the transducer is receptive to a preselected reference pressure. The transducer is of the type which produces an analog signal having a value corresponding to the difference between the airway proximal pressure and the reference pressure. The signal produced by the transducer has a first polarity when the proximal pressure is less than the reference pressure in response to an inhalation effort by the patient, and a second polarity when the proximal pressure is greater than the reference pressure in response to a exhalation effort. The invention further comprises an electromechanical mechanism, responsive to the transducer output signal, which actuates the gas-delivery device (i.e., the piston or bellows) in a manner which is determined by the polarity and value of the transducer output signal. Specifically, when the transducer output signal has the aforementioned first polarity, and an absolute value corresponding to at least a threshold level pressure differential between the airway proximal pressure and the reference pressure, the electromechanical mechanism causes the gas-delivery device to deliver gas to the patient at a flow rate which is proportional to the absolute value of the transducer output signal. Thus, the rate of gas flow to the patient is proportional to the pressure drop, with respect to the reference pressure, induced by the patient during inhalation, which pressure drop corresponds to the degree of the patient's demand for gas. The gas delivery device will, therefore, be actuated and controlled by the electromechanical mechanism in a manner which strives to meet that demand even as the demand changes during the course of inhalation.

Conversely, the aforesaid electromechanical mechanism is responsive to the second polarity of the transducer output signal so as to cause the gas-delivery device to cease its delivery of gas and to receive a fresh supply of gas from the ventilator's pressurized gas source.

Thus, when the patient breathes spontaneously, the drop in airway proximal pressure with respect to the reference pressure will cause the gas-delivery means to be actuated in such a manner as to constantly strive to neutralize the inhalation-produced pressure drop. Viewed another way, when the gas-delivery device is triggered to deliver gas in response to a signal indicative of the aforementioned threshold level pressure differential between the airway proximal pressure and the reference pressure, gas will be delivered by the gas-delivery system at a rate which is substantially proportional to the deviation of the actual pressure differential from the aforementioned threshold pressure differential, so that the system, in effect, strives to maintain the threshold level pressure differential. Once this threshold level pressure differential is achieved, actuation of the gas-delivery system is caused to cease. When the signal received by the electromechanical control mechanism either switches to the second polarity (indicating an exhalation effort), or when the signal remains at a level indicative of the threshold level pressure differential for a predetermined time interval (indicating the satifaction of the patient's demand), the gas-delivery mechanism is caused to be actuated so as to recharge itself with a fresh supply of gas.

As will be described more fully below, the electromechanical control mechanism includes an electronic servo-controlled means responsive to the pressure transducer's output signal, and operative to supply a control signal to a drive mechanism which actuates the gas-delivery mechanism in accordance with the control signal. The servo-controlled circuit includes means for adjusting the sensitivity of the system (the degree of inhalation effort which will be interpreted as a spontaneous breath attempt).

Thus, as will be understood more fully from the detailed description which follows, the present invention provides a demand regulator function in a medical ventilator, such that the ventilator is able to accommodate spontaneous patient breathing in a manner which closely resembles the normal breathing that the patient would experience unattached to the ventilator. Moreover, this function is provided with a mechanism which is greatly simplified as compared to prior-art systems which provide such a function, with the advantages normally attendant to mechanical simplification.

BRIEF DESCRIPTION OF THE DRAWING

The single FIGURE is a schematic diagram of a volume ventilator employing a demand regulator system in accordance with the present invention.

DETAILED DESCRIPTION OF THE INVENTION

The present invention is described herein in conjunction with a volume ventilator of a particular configuration. However, it should be understood that the present invention is easily adaptable for use with a wide variety of medical ventilators of the type employing a positive displacement gas-delivery system (i.e., a piston or a bellows), and which have provision for spontaneous breathing.

In the volume ventilator illustrated in the FIGURE, air and oxygen are respectively fed through a pair of regulators 10 and 12 and delivered to a blending or mixing device 14, where the gases are mixed to a proportion suitable for breathing by a patient (represented schematically and designated by the numeral 16). From the mixing device 14, the blended gas is delivered through a check valve 18 to an inlet 20 of a chamber or cylinder 22 of predetermined maximum volume. Operatively disposed within the cylinder 22 is a piston 24, the latter being actuated so as to reciprocate back and forth within the cylinder 22 by an electromechanical piston drive mechanism 26, of a type well-known in the art. (It should be well understood that, although a piston is disclosed as preferred, a bellows could easily be employed with minor mechanical modifications.) The cylinder 22 has an outlet 28 which communicates, via a check valve 30, with a inhalation conduit 32. Gas is delivered from the inhalation conduit 32 to the patient 16 via a suitable patient connection such as an endotracheal tube 34.

As will be described in further detail below, the cylinder 22 and piston 24 provide both a demand regulator function during spontaneous breathing and a breath-assist function when the ventilator is in its assist mode. In either case, the withdrawal of the piston 24 from the cylinder 22 causes the cylinder 22 to be charged with a supply of gas from the mixing apparatus 14 via the check valve 18 and the inlet 20. This may be called the "negative pressure stroke" of the piston. When the piston 24 is caused to move forward within the cylinder 22 (i.e., the "positive pressure stroke"), the gas if forced out of the outlet 28, through the check valve 30 and into the patient's lungs via the inhalation conduit 32 and the endotracheal tube 34. Typically, the gas in the inhalation conduit 32 is advantageously treated by a humidifier 36. A filter (not shown) may also be provided in the inhalation conduit 32 to remove dust and bacteria.

Also connected to the endotracheal tube 34 is an exhalation conduit 38 having an outlet port 40 enclosed within a variable pressure chamber 42, one wall of which forms a diaphragm 44 in registry with the outlet port 40. An exhalation control piston 46 is located with respect to the diaphragm 44 so as alternately to flex the diaphragm to a position blocking the outlet port 40 when the piston 46 is in a forward position, and to release the diaphragm 44 and allow gas to flow out of the exhalation conduit 38 through the outlet port 40 when the piston 46 is in a retracted position. A piston control device 48, such as a solenoid, is under the control of an output signal received from an assist control circuit, via line 51, in a manner to be described presently.

The variable pressure chamber 42 communicates with a reference pressure chamber 52 through a check valve 54 that permits gas flow only from the chamber 42 to the chamber 52. The pressure within the reference pressure chamber 52 is positively maintained at a constant level by means of a gas jet source 56 that delivers a steady jet stream through a venturi 58 and into the chamber 52. A number of outlet orifices 60 are located between the gas jet source 56 and the venturi 58 to allow gas exhaled by the patient to exit from the ventilator system. The gas jet source 56 is adjustable within a range that permits the pressure inside the reference pressure chamber 52 to be set between approximately zero and fifteen centimeters of water (cmH$_2$O) gauge. A bleeder line 62 enables a backflow of gas from the reference pressure chamber 52 to enter the variable pressure chamber 42, with an adjustable valve 64 forming a restriction in the line 62 to limit the flow rate. The valve 64 may be adjusted between fully opened and fully closed positions.

Dynamic control of the ventilator, both in its assist and spontaneous modes, begins with a differential pressure transducer 65. The transducer 65 is of a type which produces an analog electrical signal having an absolute value which is proportional to the magnitude of the pressure differential applied across the transducer, and a polarity which is indicative of the sign of that pressure differential (i.e., whether the pressure at a first pressure sensing input is greater than or less than the pressure at a second pressure sensing input). Thus, the transducer 65 has a first side or pressure sensing input which receives the patient's airway proximal pressure from the conduit 38 via the variable pressure chamber 42 by means of a conduit 66, and a second side or pressure sensing input receptive to the pressure in the reference pressure chamber 52 via a conduit 68. The transducer 65 has an electrical output line 70 which provides an electrical connection both to the assist control circuit 50 via a switch 72, and to a spontaneous breath servo circuit 74, via a branch line 76.

It can thus be seen that the first side of the pressure transducer 65 receives a variable, patient induced pressure via the exhalation conduit 38, variable pressure chamber 42, and first pressure input conduit 66 (assuming that the exhalation conduit outlet port 40 is uncovered by the diaphragm 44). The other side of the transducer receives, via the second pressure input conduit 68, the pressure from the reverence pressure chamber 52, which is maintained at a substantially constant level, thereby providing a substantially constant reference pressure. With this arrangement, the transducer 65 will produce an output signal having a first polarity, indicative of incipient or ongoing inhalation, when the pressure in the variable chamber 42 (which is proportional to the airway proximal pressure of the patient) is less than the reference pressure in the chamber 52. Conversely, the transducer 65 will provide an output signal of a second polarity, indicative of incipient or ongoing exhalation, when the pressure in the chamber 42 exceeds that in chamber 52. In either case, the magnitude of the transducer output signal will be proportional to the magnitude of the pressure differential between the two chambers. When the pressures in the two chambers are approximately equal, indicating a quiescent phase between inhalation and exhalation, the transducer 65 will yield a null signal. When the pressure in the variable pressure chamber 42 exceeds the pressure in the reference pressure chamber 52 by a predetermined threshold amount, the transducer 65 produces a signal having the first polarity and an absolute value which exceeds a predetermined signal threshold value. The signal so produced is transmitted to the assist control circuit 50 and to the spontaneous breath servo circuit 74 over the lines 70 and 76. The two latter circuits will then be actuated in a manner to be subsequently described.

It should be understood that the reference pressure chamber 52 may, in practice, be any source of a substantially constant reference pressure, preferably an adjustable one. However, for the sake of completeness of the disclosure, the chamber 52 is shown and described in conjunction with an exhalation apparatus of the type disclosed in U.S. Pat. No. 3,903,881 to Weigl and U.S. Pat. No. 4,141,356 to Smargiassi, both of these patents being commonly assigned with the present application. The purpose of this exhalation apparatus is threefold: (1) to establish an adjustable positive end expiratory pressure (PEEP); (2) to provide an adjustable reference pressure to the transducer 65 to control the action of the ventilator; and (3) to compensate for any leakages which may occur at the interface between the endotracheal tube 34 and the patient 16.

Briefly described, the reference pressure generating apparatus operates as follows: The setting of the adjustable valve 64 is normally determined by the expected voluntary inhalation flow rate produced by the patient. Gas flows through the bleeder line 62 should be substantially unrestricted by the valve 64 for flow rates that are substantially less than the expected inhalation rate. At such low flow rates, the flow through the bleeder line 62 is sufficient to substantially equalize the pressures in the chambers 42 and 52, thereby causing the pressure transducer 65 to produce a null signal. Larger backflows of gas are established from the chamber 42 to the patient 16 through the exhalation conduit 38 when the patient attempts to inhale. When this occurs, the flow of gas through the bleeder line 62 is restricted by the valve 64 to a rate less than that which is necessary to equalize the pressures in the chambers 42 and 52, thereby producing a pressure differential between the two chambers that causes the transducer 65 to produce an electrical signal having the first polarity indicative of an inhalation attempt.

An inhalation attempt which yields at least the predetermined threshold level pressure differential between the chambers 42 and 52 results in the generation, by the transducer 65, of an electrical signal having the aforesaid first polarity and a magnitude proportional to the pressure differential. This signal is applied to the assist control circuit 50 and the spontaneous breath servo circuit 74 over the lines 70 and 76. The assist control circuit 50 may be any of a variety of types which actuate the piston 24, via the piston drive mechanism 26, so as to deliver an assisted breath in accordance with some predetermined regimen. An example of such a control circuit is disclosed in the aforementioned patent to Smargiassi. Thus, for example, the control circuit 50 may be one which provides an actuation signal to the piston drive mechanism 26 after the reception of a programmable number of signals indicative of inhalation attempts from the transducer 65. When the predetermined number of inhalation attempts are sensed by the transducer 65, via the pressure differentials established between the chambers 42 and 52, the control circuit 50 transmits an actuation signal to the piston drive mechanism 26 over a line 78, thereby causing the piston 24 to deliver an assisted breath to the patient with a positive pressure stroke, as described above. Simultaneously, the control circuit 50 transmits a signal over line 51 to the exhalation piston control mechanism 48, which causes this mechanism to actuate the exhalation piston 46 so as to press the diaphragm 40 into a blocking engagement against the outlet port 40. At the end of the positive pressure stroke, the piston 24 is caused to withdraw so as to refill the cylinder 22 with a fresh gas supply.

Any breath attempt which does not initiate an actuation signal by the assist control circuit 50 may be considered the initiation of a spontaneous breath by the patient. The output signal of the pressure transducer 65, as previously mentioned, is an analog signal having an absolute value proportional to the magnitude of the pressure differential between the chambers 42 and 52. This output signal is received by the spontaneous breath servo circuit 74 over the line 76. The servo circuit 74 will be enabled in response to an indicated spontaneous breath attempt. Such an attempt will be indicated by a signal over the line 76 having the aforementioned first polarity and an absolute value at or above a predetermined threshold value, which may be the same as or greater than the threshold value used to actuate the assist control 50. Upon the receipt of such a signal from the transducer 65, the servo circuit 74 will produce an electrical control signal which is fed along a line 80 to the piston drive mechanism 26. When the servo circuit 74 receives a spontaneous breath attempt signal, the control signal transmitted over line 80 will have a magnitude proportional to the value of the input signal received from the pressure transducer 65. The piston drive mechanism 26 is such that it drives the piston 24 forward, in a positive pressure stroke, with a speed which is proportional to the absolute value of the signal received from the servo circuit 74. Thus, the piston 24 is driven so as to displace gas from the cylinder 22 at a rate which is directly proportional to the absolute value of the transducer output signal. As previously described, the transducer output signal has an absolute value which is directly proportional to the pressure differential between the chambers 42 and 52, which pressure differential is, in turn, a direct function of the patient's instantaneous inhalation effort. Thus, the piston 24 is caused to displace gas from the cylinder 22 into the inhalation conduit 32, and from there to the patient at a rate which is an almost instantaneous function of the patient's demand. In other words, the piston 24 is, in effect, "slaved" to the patient's demand, in that it strives to deliver gas at a rate which is sufficient to compensate for the deviation from the threshold level pressure differential caused by the patient's instantaneous inhalation effort. In short, the action of the servo circuit 74, in conjunction with the drive mechanism 26, is such as to cause the delivery of gas by the piston 24 at a rate which substantially maintains the threshold level pressure differential. As the patient's demand is gradually satisfied, the piston's action will be slowed so that the rate of gas flow from the cylinder 22 is decreased. When the patient's demand has decreased to the point that the pressure differential between the two chambers 42 and 52 reaches the aforementioned threshold pressure differential, the pressure transducer 65 yields the threshold level output signal, which causes the servo circuit 74 to respond by means of a control signal along the line 80, having a first predetermined value such that the drive mechanism stops the action of the piston.

It is, of course, necessary to recharge the cylinder 22 with a fresh supply of gas via the inlet 20 after a predetermined interval of time following the cessation of inhalation, or upon the initiation of exhalation, whichever first occurs. To achieve this end, the piston 24 must be actuated to undergo a "negative pressure stroke" (i.e., a withdrawal from the cylinder 22) at the appropriate time. This function is also accomplished by the spontaneous breath servo circuit 74, in the following manner:

As previously mentioned, an exhalation attempt will result in a transducer output signal having the second polarity being transmitted over lines 70 and 76. In response to this second polarity signal, the servo circuit 74 transmits a control signal over line 80 having a second predetermined value, such that the drive mechanism 26 causes the piston 24 to undergo a negative pressure stroke. If, however, the aforementioned predetermined time interval (as measured by, e.g., a conventional "clock circuit" within the servo circuit 76) has elapsed, the servo circuit 74 will transmit a control signal having the second predetermined value, even if the second polarity signal has not been received from the transducer 65. In either case, the cylinder 22 is recharged and ready to deliver either a spontaneous breath or an assisted breath, depending upon the type of command received by the drive mechanism 26.

It should be noted that when the control circuit 50 calls for an assisted breath, as previously described, it is desirable to disable the spontaneous breath servo circuit 74 so that the drive mechanism 26 cannot receive a potentially confusing signal from the latter circuit. This is accomplished by having the control circuit 50 transmit a blocking or disabling signal to the servo circuit 74 over a line 82 when the control circuit 50 actuates the assist mode.

In some circumstances, it may be desirable to disable the control circuit 50, so that the ventilator performs only in the spontaneous breathing mode, i.e., as a demand regulator. This is accomplished by opening the switch 72, thereby electrically isolating the control circuit 50 from the transducer 65, so that the former cannot be triggered by the latter to yield an assist mode actuation signal over the line 78, as previously described.

It may also be desirable to vary the level of the transducer output signal which is perceived by the servo circuit 74 as the aforementioned threshold value which results in the actuation of the spontaneous breathing mode. A convenient way of doing this without varying the reference pressure in the chamber 52 is to provide a sensitivity adjustment control 84 for the servo circuit 74. Such a control can assume any of a variety of types well-known in the art.

There has thus been described an improved medical ventilator apparatus which provides for both spontaneous and assisted breathing utilizing but a single-breath delivery mechanism, as well as a single drive mechanism for the delivery mechanism. Thus, both modes of operation are accommodated in an overall system which is both economical to manufacture and efficient in operation. In addition, by virtue of the present invention, good coordination between the two operational modes is maintained, if not enhanced, while also providing an advantageous degree of flexibility of operation, so that a wide range of clinical needs can be met.

What is claimed and desired to be secured by Letters Patent of the United States is:

1. A respiratory ventilator, of the type having breathable gas supply means, exhalation valving means, conduit means adapted for transmitting breathable gas to a patient during inhalation and for transmitting exhaled gas from said patient to said exhalation valving means, and gas-delivery means for alternately receiving gas from said gas supply means during exhalation and delivering said received gas to said conduit means during inhalation, wherein the improvement comprises:

first means for supplying a reference pressure;

second means, receptive to said reference pressure and the pressure in said conduit means, for producing an electronic signal having a value indicative of the pressure differential between said first means and said conduit means, said electronic signal having a first polarity when the pressure in said conduit means is less than said reference pressure in response to an inhalation effort by said patient, and a second polarity when the pressure in said conduit means exceeds said reference pressure in response to an exhalation effort by said patient; and third means, responsive to said electronic signal, for (a) actuating said gas-delivery means so as to deliver gas to said conduit means at a rate which is substantially proportional to the absolute value of said electronic signal when said electronic signal has said first polarity and a predetermined threshold value indicative of at least a threshold level pressure differential, and (b) actuating said gas-delivery means so as to receive gas from said gas supply means either when said electronic signal has said second polarity or when said electronic signal remains approximately at said predetermined threshold value for a predetermined time interval, whichever first occurs.

2. The improvement of claim 1, wherein said rate of gas delivery by said gas-delivery means to said conduit means is such as substantially to maintain said threshold level pressure differential.

3. The improvement of claim 1, wherein said third means comprises:

control means for (a) producing a first output signal in response to said electronic signal when said electronic signal has said first polarity and a value at least approximately equal to said predetermined threshold value, said first output signal having a value substantially proportional to the value of said electronic signal, and (b) producing a second output signal in response to said electronic signal when said electronic signal has said second polarity, or when the value of said electronic signal remains approximately equal to said threshold value for said predetermined time interval, whichever first occurs; and actuation means, responsive to said first and second output signals, for respectively (a) actuating said gas-delivery means so as to deliver gas to said conduit means at a rate which is substantially proportional to the value of said first output signal, and (b) actuating said gas-delivery means so as to receive gas from said gas supply means in response to said second output signal.

4. The improvement of claim 1, further comprising:
fourth means, operatively associated with said third means, for selectively varying said predetermined threshold value of said electronic signal.

5. The improvement of claim 1, wherein said second means comprises a differential pressure transducer having a first pressure-sensing inlet in communication with said first means and a second pressure-sensing inlet in communication with said conduit means.

6. The improvement of claim 1, further comprising:
assisted breath delivery means, responsive to said electronic signal, for (a) actuating said gas-delivery means so as to deliver gas to said conduit means at a predetermined rate in response to selectable instances of said first polarity in said electronic signal, and (b) substantially simultaneously disabling said third means.

7. The improvement of claim 6, wherein said assisted breath delivery means produces an electrical signal indicative of the actuation of said gas-delivery means by said assisted breath delivery means, and further comprising:
means, responsive to said electrical signal, for closing said exhalation valving means.

8. A demand regulator for delivering breathable gas to a living subject capable of spontaneous respiration, comprising:

first means for alternately receiving a supply of breathable gas from a source and delivering all or part of said received supply to said subject;

second means for supplying a reference pressure;

pressure transducing means, having first and second pressure inputs, and receptive to said reference pressure and the airway proximal pressure of said subject, for producing an electronic signal having a value proportional to the difference between said reference pressure and said airway proximal pressure, said electronic signal having a first polarity when said airway proximal pressure is less than said reference pressure in response to an inhalation effort by said subject, and a second polarity when said airway proximal pressure is greater than said reference pressure in response to an exhalation effort by said subject;

third means, responsive to said electronic signal, for (a) producing a first output signal when said electronic signal has said first polarity and a value greater than a predetermined threshold value indicative of a threshold level differential between said airway proximal pressure and said reference pressure, said first output signal having a value substantially proportional to the value of said electronic signal, (b) producing a second output signal when said electronic signal has a value substantially equal to said threshold value, and (c) producing a third output signal when said electronic signal has said second polarity or when said electronic signal remains substantially at said threshold value for a predetermined time interval, whichever first occurs;

fourth means, for (a) actuating said first means in a first mode in response to said first output signal so as to deliver gas to said subject at a rate which is substantially proportional to the absolute value of said first output signal, (b) ceasing the actuation of said first means in response to said second output signal, and (c) actuating said first means in a second mode in response to said third output signal so as to receive a fresh supply of gas from said source;
an exhalation valve;
first conduit means for transmitting gas from said first means to said subject during said first mode;
second conduit means for transmitting exhaled gas from said subject to said exhalation valve during said second mode, said second conduit means being receptive to said airway proximal pressure;
first pressure communication means for communicating said airway proximal pressure from said second conduit means to said first pressure input; and
second pressure communication means for communicating said reference pressure from said second means to said second pressure input.

9. The demand regulator of claim 8, further comprising:
fifth means, operatively associated with said third means, for selectably varying said predetermined threshold value of said electronic signal.

10. The demand regulator of claim 8, further comprising:
means for selectably varying said reference pressure.

11. The demand regulator of claim 8, wherein said first means comprises:
a chamber having an inlet adapted for fluid communication with said source and an outlet adapted for fluid communication with said subject;
means responsive to said fourth means for alternately forcing gas out of said chamber through said outlet in said first mode and drawing gas into said chamber through said inlet in said second mode; and
valving means, operatively associated with said inlet and said outlet, for allowing gas to flow through said inlet substantially only from said source and through said outlet substantially only toward said subject.

12. The demand regulator of claim 11, wherein said chamber comprises a cylinder of fixed maximum volume, and said means responsive to said fourth means comprises a piston adapted for movement into said cylinder during said first mode at a rate which is substantially proportional to the value of said first output signal, and for withdrawal from said cylinder during said second mode.

13. A respiratory ventilator, of the type including breathable gas supply means, exhalation valving means, conduit means adapted for transmitting breathable gas to a patient during inhalation and for transmitting exhaled gas from said patient to said exhalation valving means, and gas-delivery means for alternately receiving gas from said gas supply means during exhalation and delivering said received gas to said conduit means during inhalation, wherein the improvement comprises:
first means for supplying a reference pressure;
transducing means, having a first pressure input in fluid communication with said conduit means and a second pressure input in fluid communication with said first means, for producing an analog signal having a value proportional to the difference between said reference pressure and the pressure in said conduit means, said analog signal having a first polarity when said pressure in said conduit means is less than said reference pressure in response to an inhalation effort by said patient, and a second polarity when said pressure in said conduit means is greater than said reference pressure in response to an exhalation effort by said patient;
first control means, responsive to said analog signal, for (a) producing a first control signal when said analog signal has said first polarity and a value greater than a predetermined threshold value indicative of a threshold level differential between said pressure in said conduit means and said reference pressure, said first control signal having a value substantially proportional to the value of said analog signal, (b) producing a second control signal when said analog signal has a value substantially equal to said threshold value, and (c) producing a third control signal when said analog signal has said second polarity or when said analog signal remains substantially at said threshold value for a predetermined time interval, whichever first occurs;
second control means, responsive to said analog signal, for (a) producing a fourth control signal in response to selectable instances of said first polarity in said analog signal, and (b) substantially simultaneously disabling said first control means; and
actuation means for (a) actuating said gas-delivery means in a first mode in response to said first control signal so as to deliver gas to said conduit means at a ratio which is substantially proportional to the absolute value of said first control signal, (b) ceasing the actuation of said gas-delivery means in response to said second control signal, (c) actuating said gas-delivery means in a second mode in response to said third control signal so as to receive a fresh supply of gas from said source, and (d) actuating said gas-delivery means in a third mode in response to said fourth control signal so as to deliver gas to said conduit means at a predetermined rate.

14. The improvement of claim 13, further comprising meas for selectably disabling said second control means.

15. The improvement of claim 13, further comprising means, operatively associated with said first control means, for selectably varying said threshold value of said analog signal.

16. A method of operating a piston or a bellows to deliver breathable gas to a subject capable of spontaneous breathing during a period of inhalation by said subject, and to receive a fresh supply of said gas from a source thereof during a period of exhalation by said subject, said method comprising the steps of:
(1) supplying a reference pressure;
(2) comparing the airway proximal pressure of said subject to said reference pressure;
(3) actuating said piston or bellows so as to deliver said gas to said subject at a rate which is substantially proportional to the difference between said airway proximal pressure and said reference pressure when said reference pressure exceeds said airway proximal pressure by at least a predetermined pressure differential indicative of an inhalation attempt by said subject;
(4) actuating said piston or bellows so as to receive a fresh supply of gas from said source when said airway proximal pressure exceeds said reference pressure, thus indicating an exhalation effort by said subject;
(5) selecting predetermined ones of said inhalation attempts in accordance with a predetermined program; and
(6) actuating said piston or bellows so as to deliver said gas to said subject at a predetermined rate in response to the detection of said selected inhalation attempts.

* * * * *